(12) United States Patent
Jung et al.

(10) Patent No.: US 8,680,311 B2
(45) Date of Patent: Mar. 25, 2014

(54) MONOLITHIC ELECTROKINETIC PUMP FABRICATION

(75) Inventors: Moon Chul Jung, Marlborough, MA (US); Edouard S. P. Bouvier, Stow, MA (US); Steven A. Cohen, Hopkinton, MA (US); Hua Yang, Franklin, MA (US)

(73) Assignee: Waters Technologies Corporation, Milford, MA (US)

( * ) Notice: Subject to any disclaimer, the term of this patent is extended or adjusted under 35 U.S.C. 154(b) by 856 days.

(21) Appl. No.: 12/447,477

(22) PCT Filed: Nov. 6, 2007

(86) PCT No.: PCT/US2007/083803
§ 371 (c)(1),
(2), (4) Date: Jan. 12, 2010

(87) PCT Pub. No.: WO2008/136854
PCT Pub. Date: Nov. 13, 2008

(65) Prior Publication Data
US 2010/0168457 A1 Jul. 1, 2010

Related U.S. Application Data

(60) Provisional application No. 60/864,737, filed on Nov. 7, 2006.

(51) Int. Cl.
*C07F 7/00* (2006.01)

(52) U.S. Cl.
USPC .......................................................... 556/425

(58) Field of Classification Search
USPC .......................................................... 556/425
See application file for complete search history.

(56) References Cited

U.S. PATENT DOCUMENTS

| | | | |
|---|---|---|---|
| 5,623,026 A | 4/1997 | Buekers et al. | |
| 6,277,257 B1 | 8/2001 | Paul et al. | |
| 6,515,043 B2 | 2/2003 | Petty et al. | |
| 2003/0213732 A1* | 11/2003 | Malik et al. | 210/94 |
| 2004/0129141 A1* | 7/2004 | Malik et al. | 96/101 |
| 2004/0208751 A1 | 10/2004 | Lazar et al. | |
| 2005/0051430 A1 | 3/2005 | Shepodd et al. | |
| 2005/0139536 A1* | 6/2005 | Belov et al. | 210/198.2 |
| 2005/0161334 A1 | 7/2005 | Paul | |
| 2005/0220681 A1 | 10/2005 | Chang et al. | |
| 2005/0230298 A1* | 10/2005 | Jiang et al. | 210/198.2 |
| 2005/0247558 A1 | 11/2005 | Anex et al. | |
| 2005/0252776 A1 | 11/2005 | Mosier et al. | |
| 2006/0040509 A1 | 2/2006 | Yim et al. | |
| 2006/0065529 A1 | 3/2006 | Schlenoff et al. | |
| 2006/0180549 A1 | 8/2006 | Liu et al. | |

FOREIGN PATENT DOCUMENTS

JP          07-247180         9/1995

OTHER PUBLICATIONS

Yan, L. et al. "Hybrid organic-inorganic monolithic stationary phase for acidic compounds separation by capillary electrochromatography," J. Chromatog. A, (2004) 1046: 255-261.*
Yan, L. et al. "Hybrid organic-inorganic phenyl monolithic column for capillary electrochromatography," Electrophoresis (2005) 26: 2935-2942.*
Razunguzwa, Trust T. et al; Fabrication and Characterization of a Fritless Microfabricated Electroosmotic Pump With Reduced pH Dependence; Anal. Chem. Mar. 1, 2004, 76, pp. 1336-1341.
Chen, Zilin et al; An electro-osmotic micro-pump based on monolithic silica for micro-flow analyses and electro-sprays; Anal Bioannal Chem (2005) 383; 817-824.
Tripp, Jennifer A.; High-pressure electroosmotic pumps based on porous polymer monoliths; Sensors and Actuators B 99 (2004) pp. 66-73.
Zeng, Shulin; Fabrication and characterization of electroosmotic micropumps; Ssensors and Actuagors B 79 (2001) pp. 107-114.
Chen, Chuan-Hua; A Planar Electroosmotic Micropump; Journal of Microelectromechanical Systems, vol. 11, No. 6, Dec. 2002.
Zeng, Shulin et al; Electroosmotic flow pumps with polymer frits; Sensors and Actuators B 82 (2002) pp. 209-212.
Wang, Ping et al; A new electro-osmotic pump bases on silica monoliths; Sensors and Actuators B 113 (2006) pp. 500-509.
Hasselbrink, Jr.,; Ernest F. et al; High-Pressure Microfluidic Control in lab-on-a-Chip Devices Using Mobile Polymer Monoliths; Anal. Chem 2002, 74, 4913-4918.
Chen, Zilin; Electrokinetic microfluidic applications of monolithic silica material; The 230th national Meeting, in Washington, DC ; Aug. 28-Sep. 1, 2005.

* cited by examiner

*Primary Examiner* — Johann R Richter
*Assistant Examiner* — Kofi Adzamli
(74) *Attorney, Agent, or Firm* — Nielsen IP Law LLC (57) ABSTRACT

High-pressure electrokinetic ("EK") pumps comprising a hybrid monolith provide a high surface charge density and a continuous stable skeleton morphology with micrometer-sized through-pores. The hybrid monolith of the subject invention has superior mechanical strength and better stability in comparison to prior art monoliths with equivalent mechanical stability. The surface charge of the hybrid monolith can be modified and/or made stable by the use of different chemical reagents. The chemical reagents and resulting modification to the monolith serves to expand the usefulness of the hybrid monolith to a variety of pumping applications including chip-based systems and other applications where the ability to pump an acidic solution is required.

3 Claims, 8 Drawing Sheets

FIG. 6B
After surface grafting

FIG. 6A
Before surface grafting

FIG. 7

MONOLITHIC ELECTROKINETIC PUMP FABRICATION

CROSS REFERENCE TO RELATED APPLICATIONS

This application is the National Stage of International Application No. PCT/US2007/83803, filed on 6 Nov. 2007 and designating the United States, which claims benefit of a priority from U.S. Provisional Patent Application No. 60/864,737 filed 7 Nov. 2006.

FIELD OF THE INVENTION

The present invention is directed to EK pumps particularly EK pumps comprising hybrid monoliths.

CROSS-REFERENCE TO RELATED APPLICATIONS

None.

STATEMENT REGARDING FEDERALLY SPONSORED RESEARCH OR DEVELOPMENT

None.

THE NAMES OF THE PARTIES TO A JOINT RESEARCH AGREEMENT

None.

REFERENCE TO SEQUENCE LISTING

None.

BACKGROUND OF THE INVENTION

Micro-electromechanical system technology has spurred the development of different types of micro-pumps to transport liquids over a wide range of flow rates and pressures. Micro-pumps basically fall into one of two groups: membrane displacement pumps and field-induced flow pumps. In membrane displacement pumps, the deflection of a membrane provides the pressure for pumping liquid. Conversely, field-induced pumps operate via electroosmotic flow ("EOF"). Field-induced pumps have an important advantage in that this type of pump does not require moving parts that complicate fabrication and sealing.

In an electrokinetic ("EK") pump, also known as an "electroosmotic pump," precise flow control is driven by an applied electric field and achieved simply with current or a voltage-controlled circuit. In such pumps, the potential is applied at the ends of the capillary and viscous drag creates EOF. Fluid migrates towards positive electrode in positive pumps and towards the negative electrode in negative pumps.

By design, EK pumps have low stall pressure. Generally, prior art open channel and capillary EK pumps are not used in systems with high-pressure loads. Unlike mechanical pumps, electroosmotic flow does not produce a pressure field. In order to achieve high pressure, the pump channel must be very small to produce hydrodynamic resistance. This is opposite of a mechanical pump where hydrodynamic resistance reduces the flow and build up of high pressure. However, in the EK pump, the hydrodynamic resistance effects a reduction in the fluid flow in the direction opposite that of electroosmotic flow; this results in a net build-up of pressure at the channel outlet. Hence, pump channels need to be as small as possible, but not smaller than the double layer thickness of the electrolyte. Moreover, because a single small pump channel limits the maximum flow, a large bundle of micro-channels is needed.

Conventional EK pumps, both open channel and capillary, can fail as a result of bubble generation. For example, in an open channel system, when the applied electrode potential exceeds a certain threshold voltage, bubbles are generated as a result of electrolysis and other electrode reactions. Ions are produced that contaminate the sample and block the micro-channels. To eliminate blockage, a bubble releasing device must be used downstream of the pump or bubbles must be allowed to escape via open reservoirs. If an open reservoir is used, the housing must be capable of electric field penetration. If the EK pump performance can be improved, as measured by the "EK factor", defined as the maximum pressure achieved for a given applied voltage ("psi/V") in a closed channel, then fewer bubbles will be generated without the need for such bubble releasing devices.

Attempts have been made to reduce the electrode reaction and low-pressure disadvantages of the EK pump. One approach has been to pack capillaries or channels with small particles containing high surface charge that still allows for electro-osmotic flow. However, packing the column is very difficult, particularly when particles less than ca. 1 micron diameter are used. With such particles, extremely high pressures are required, which often cannot be obtained due to the limitations in mechanical strength of the device. In addition, long times are required to pack such columns, which can add substantially to the cost of the device.

Hence, monoliths have been recently been considered for use as components in high-pressure EK pumps. Monoliths have been synthesized using organic and inorganic materials and combinations thereof. While organic materials are chemically stable under alkaline and acidic conditions, these materials shrink and swell when subjected to different solvents. In addition, they do not have the mechanical strength of inorganic silica materials. On the other hand, silica-based monoliths suffer from shrinkage during synthesis and large voids between the monolith and the capillary wall/channel wall can result.

EK pumps using monolithic compositions have been suggested. See e.g., U.S. Pat. No. 6,290,909, col. 3 at line 36 where polymer monoliths are selected to resist pressure-driven flow and allow electroosmotically-driven flow. These monolithic compositions, however, lack rigidity and small domain size needed for high pressures. They also contain significant meso-porosity which would limit their performance as EK pumps due to the double-layer overlap which occurs in the mesopores.

Further, hybrid inorganic-organic monolith materials have been investigated as chromatographic stationary phases to improve adhesion of the monolith to the capillary wall and increase resistance to shrinkage. See e.g., WO 2004/105910. However, these materials contain significant meso-porosity which would limit their performance as EK pumps due to the double-layer overlap which occurs in the mesopores.

A need exists, therefore, for an EK monolithic pump that can produce higher pressures over a wide range of pH while maintaining a strong and stable morphology over a long lifetime.

BRIEF SUMMARY OF THE INVENTION

The present invention is directed to high-pressure electrokinetic ("EK") pumps comprising an organo-silica monolith, also referred to herein as the "hybrid monolith." EK pumps of the subject invention use electroosmotic flow to provide a high-pressure pump that uses no moving parts. The compact nature of the EK pump provides an ability to construct a capillary or microchip based High Pressure Liquid Chromatography ("HPLC") system.

The disclosed hybrid monolith has superior strength, stability, and high-pressure capability to provide reliable flow delivery and long life. As further provided, the surface charge of the hybrid monolith can be modified and/or made permanent in an effort to expand the usefulness of the EK pump to a variety of applications including pumping acidic reagents. The EK pump is compatible with and can be integrated into chip-based and other microfluidic systems.

The EK pump comprises a monolith having a continuous, stable, macroporous skeleton with pore sizes less than 1 micron and is suitable for high pressure applications. Specifically, the EK pump of the subject invention can generate pressures as high as about 20,000 psi in an acidic environment of pH of 2 or greater. The pore sizes of the monolith can be less than 1 micron. These high performance EK pumps produce at least 3 to 4 psi per volt and use low current in acetic acid eluent.

Methods for improved fabrication and reproducibility are further provided. Fabrication and preparation of the subject EK monolith pump is a one-step chemical process by applying the principles of the sol-gel chemistry together with the structure-property relationships of the resulting methylsilsesquioxanes ("MSQs"). Novel improvements in the methodology of making a monolith are directed toward reducing pore size, increasing the stability of the morphology of the monolith, increasing hydraulic flow resistivity, operating under a wide variety of pH and the ease of manufacture. Surface grafting may also be utilized for acidic EK pumps to introduce a permanent charge to the monolith.

DETAILED DESCRIPTION OF THE INVENTION

The present invention is directed to high-pressure electrokinetic ("EK") pumps comprising a hybrid monolith. Hybrid monoliths provide a high surface charge density and a continuous stable skeleton morphology with micrometer-sized through-pores. The hybrid monolith of the subject invention has superior mechanical strength to polymer monoliths and better stability in comparison to prior art monoliths with equivalent mechanical stability. As further provided herein, the surface charge of the hybrid monolith of the subject invention can be modified and/or made stable by the use of different chemical reagents. The chemical reagents and resulting modification to the monolith serves to expand the usefulness of the hybrid monolith to a variety of pumping applications including chip-based systems and other applications where the ability to pump an acidic solution is required.

Figure 1:
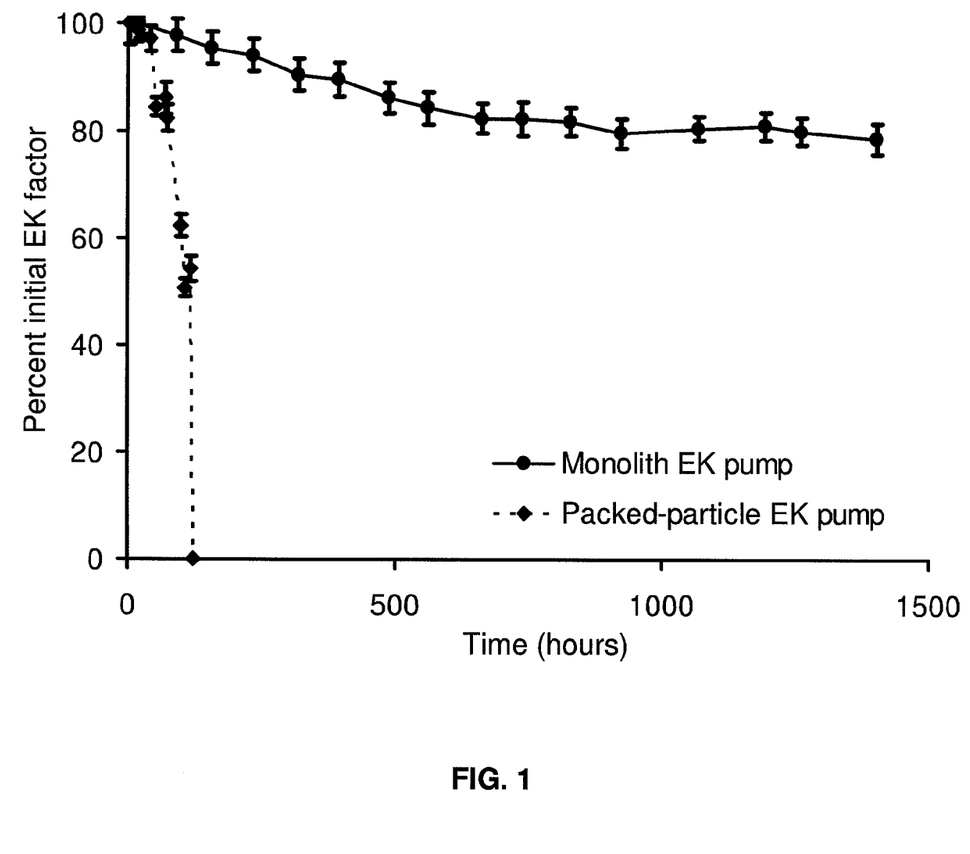
FIG. 1 provides a comparison of the EK factor of a monolith pump to a packed-bed pump.

One advantage and benefit of using the monolith pump of the subject invention is that it may be manufactured easily and efficiently. The synthesis of the monolith is a one-step process. The next step of the process is to make a monolith pump which may be generated by surface grafting. Monolith EK pumps described herein also have improved mechanical stability compared to particle-packed pump. FIG. 1 is a comparison of the lifetime with packed particle and monolithic EK pumps. As depicted in the figure, the EK factor (psi/V) of the monoliths of the present invention are compared to EK factor (psi/V) of a particle-packed pump. The pumped fluid in both cases was 0.1% acetic acid. As shown in the figures, the monolithic EK pump of the subject invention exhibits substantially longer lifetime. Basically, this means that the monolith EK pump retained its pressure capability (expressed in terms of EK factor) and remains unchanged compared to the packed-bed EK pump which shows significant losses in performance over the same time scale. One reason for this improved stability is that the rigid, single piece monolith is not adversely affected by electrokinetic or hydrodynamic forces acting on the bed which result in bed shifting.

The EK pumps of the present invention may be fabricated without the need for retaining elements (i.e., frits) which dramatically simplifies the manufacturing process. One of the challenges in fabricating an EK pump on a chip is the ability to pack stable beds on these devices at high pressure and to appropriately frit the inlet and outlet. Casting a monolith within the channel of a chip greatly simplifies the fabrication process. In addition, the applied pressure used to pack particles may be limited by the mechanical strength of the microfluidic device. Monoliths of the subject invention overcome all of these obstacles.

One approach to monolith synthesis is to perform polymerization in a controlled manner with an appropriate porogen such that the desired pore size is created via the process of spinodal decomposition. Initial composition and other starting conditions can affect the rate of spinodal decomposition which determines the ultimate macro-skeletal morphology. The polymerization process leads to a liquid phase separation between the porogens and resulting polymer. As polymerization continues, the polymer solidifies, or gels, to arrest the spinodal decomposition process. Following the gelation step, monoliths may be "aged" for a period of time, i.e., the polycondensation reactions are allowed to continue for an extended time period, in order to strengthen the gel. Hence, formation of the desired monolith morphology requires a careful balancing of the two simultaneously occurring processes of polymerization and spinodal decomposition. By varying the synthesis conditions, both size and the ratio of the skeleton and macropore diameter can be independently modulated over a fairly wide range. The ultimate macropore and skeleton morphology will be affected by any change in the reaction temperature, monomer concentration, water concentration, alcohol concentration and/or pH.

If polymerization occurs much faster than the rate of spinodal decomposition, no phase separation will occur. On the other hand, if polymerization occurs on a time scale much slower than that of spinodal decomposition, then the spinodal decomposition process will continue to coarsen the separated liquid phases, i.e. the characteristic lengths of each phase will grow over time. This ultimately can lead to formation of solid with isolated pores or to formation of particles. Each of the reaction variables plays a role in determining the relative rates of the polymerization and phase separation processes. It will also affect the solubility of oligomer in the liquid phase. While the exact mechanisms are not well understood, a temperature increase will reduce the viscosity, thereby, altering the onset and rate of spinodal decomposition. At the same time, reaction rates will change.

In the present invention, a monolith is prepared via polymerization of a hydrolyzable alkoxysilane monomer in a sol-gel type reaction. A silane monomer is first hydrolyzed and then condensed to produce a methylsilsesquioxane having an empirical formula of $[CH_3SiO_{3/2}]_n$. Generally, methylsilsesquioxanes can be prepared by hydrolysis and condensation of precurors of the formula $CH_3SiX_3$ where X is Cl, $OCH_3$ (Methytrimethoxysilane ("MTMS")) or $OC_2H_5$ (methyltriethoxysilane ("MTES")). Furthermore, $CH_3$ could be substituted by $CH_3$—$CH_2$ or a bridged ethyl group linking to silicon atoms ($X_3Si$—$CH_2CH_2$—$SiX_3$ where X is normally $OCH_3$ or $OCH_2CH_3$). Alternatively, $CH_3$ could be replaced by an allyl group.

Specifically, MTMS forms gels with lower cross-linking density than that of tetramethoxysilane (TMOS) derived gels. The sol-gel reaction begins with hydrolysis and slow condensation that proceeds at low temperature and low pH. In the next step, temperature is raised in order to increase the rate of polymerization. The oligomers are polymerized, e.g. via radical chain polymerization, and further condensed to form a polymerized sol-gel. Moreover, a polymerized group may react with the surface of a second material, e.g., with an anchoring a functionality group on the inner surface of the capillary.

One difficulty in forming stable porous structures is premature phase separation over a broad pH range, and fewer functional groups being available for cross-linking. While previously reported as not possible, stable porous MSQ gel materials (monoliths) having the appropriate morphology have been found useful as an EK pump. In at least one prior art methodology directed at a one step process, only transparent precipitates and/or macroscopically phase-separated resins were reported when the pH was below the isoelectric point (IEP) of the silanols. Chem. Mater. 2005, 17, 2807-2816.

If the pH of the reactant mixture is lower than the isoelectric point of MTMS, the MTMS hydrolysis is initiated from the acid catalysis. On the other hand, the pH of the reactant mixture could be much higher than the MTMS isoelectric point to initiate the hydrolysis through base catalysis, but the reactions are carried out in a different way. Methanol content (percentage in the monolith synthesis mixture) is a controlling factor in the pore size of the macropores. Lower methanol content correlates with the synthesis of monoliths with smaller macropores.

Hence, in the one-step method, hydrolysis and condensation proceeds at a single catalyst concentration using an acid, water or a base as the catalyst to achieve conditions where the pH was below, near or above the IEP of the silanol groups respectively. In a two-step method, monomer is initially reacted under acidic conditions for a set period of time. And, depending on the processing condition used, a range of different MSQ materials were obtained. Id.

The specific reaction chemistry involved in the preparation of the monolith suitable for use in present invention is:

$CH_3$—Si—$(X)_3$+$H_2O$→$CH_3$—Si—$(X)_2$(OH)+HX  Reaction (1):

$(CH_3)(X)_2$—Si—OH→$CH_3(X)_2$—Si—O—Si—$(X)_2$
$CH_3$+$H_2O$  Reaction (2):

$(CH_3)(X)(OH)$—Si(X)+(HO)Si($X_2$)($CH_3$)→$(CH_3)(X)$
$(OH)Si$—O—$Si(X)_2(CH_3)$+HX  Reaction (3):

where X is Cl, $OCH_3$, or $OC_2H_5$.

Reaction (1) is the hydrolysis step of the alkoxysilane monomer. Reactions (2) and (3) are the condensation reactions.

Noteworthy, hydrolysis does not necessarily stop with the formation of $CH_3$—Si—$(X)_2$(OH). The X groups can further hydrolyze to form $CH_3$—Si—$(X)(OH)_2$ and $CH_3$—Si—$(OH)_3$. Each one of the compounds can undergo condensation reactions.

Figure 2:
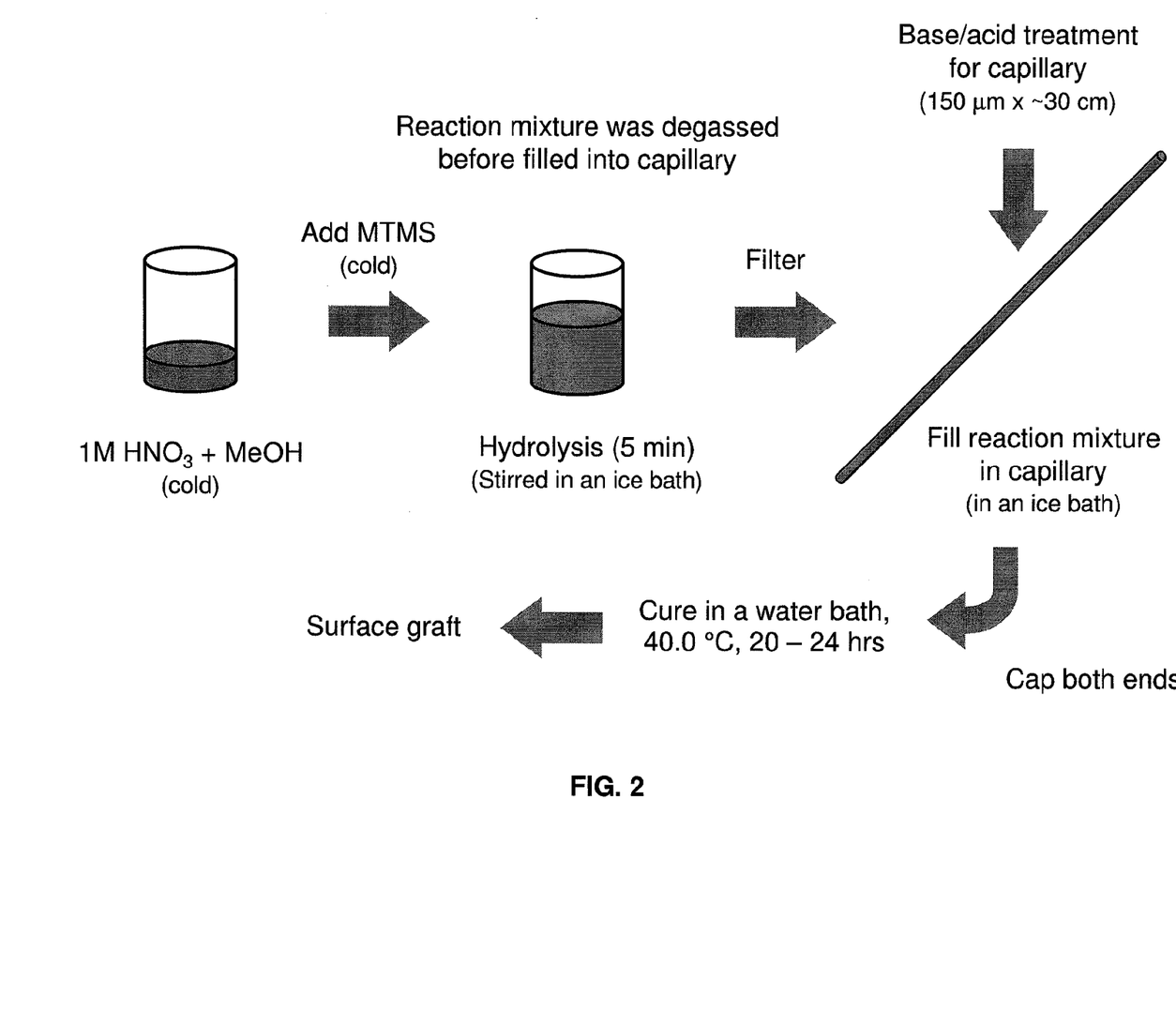
FIG. 2 is an illustration of the processing of a hybrid monolith of the subject invention.
Figure 3A:
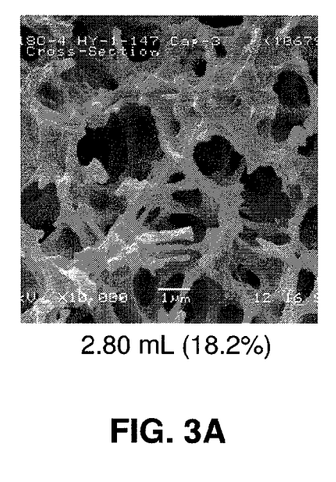
FIGS. 3A, 3B, 3C and 3D are the scanning electron microscopy images ("SEM") of monoliths prepared by different amounts of methanol used in the synthesis of the monolith.
Figure 3B:
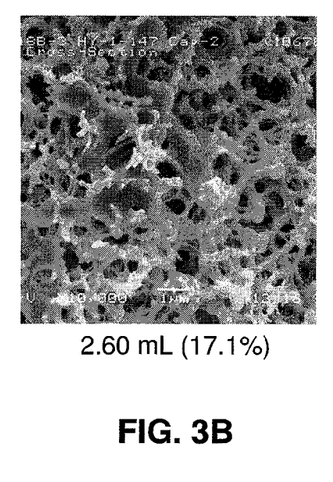
Figure 3C:
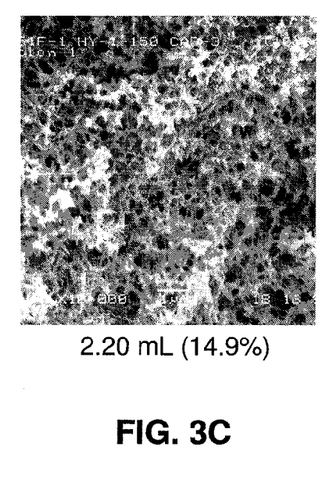
Figure 3D:
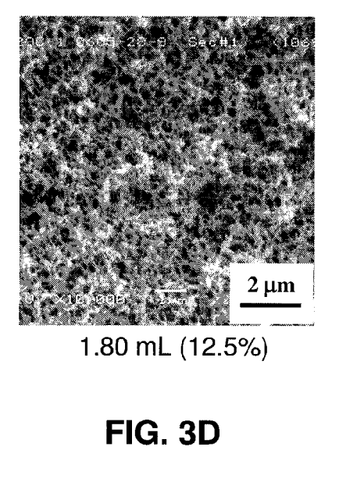

As illustrated schematically in FIG. 2, a hydrolyzable alkoxysilane monomer of the formula $CH_3$—Si—$(X)_3$, where X=Cl, $OCH_3$, or $OC_2H_5$ is mixed with an acidic catalyst and methanol, MeOH, in a container at 0 to 4° C. and maintained at 0 to 4° C. for between about 0 to 5 minutes, preferably stirred or otherwise physically mixed. Furthermore, because hydrolysis is an exothermic reaction, the solution should be placed on an ice bath or other mechanism to ensure the reaction mixture remains at a temperature between about 0 to 4° C.

The amount of methanol is the controlling factor that effects pore size. As illustrated in FIGS. 3A through 3D and described in the examples below, decreasing the methanol decreases the pore size. It changes various characteristics such as hydrolysis/polymerization rates, spinodal decomposition rates and/or gel solubility. The volume percent of methanol can be between about 10 to 18 percent. Different relative volume of each reactant changes the physical structure of the monolith and possibly pore size. The physical structure of the monolith varies with variations in the relative volume of each reactant, yielding continuous pores, isolated pores or aggregates.

Specifically, FIG. 3 depicts the cross-sectional area of monoliths fabricated using 2.80 ml methanol, 2.60 ml methanol, 2.20 ml methanol and 1.80 ml methanol in the reaction mixture. Pore sizes within the solidified polymer were controlled by the amount of methanol used. As the amount of methanol was decreased, the pores became smaller and possibly are more uniformly oriented. Alternatives to use of methanol may include ethanol and similar organic solvents.

One reaction catalyst is nitric acid $HNO_3$. However, any acid may be suitable as a catalyst including but not limited to HCl, HBr, HI, $HClO_4$, $H_2SO_4$, acetic acid, benzoic acid, chloroacetic acid, chlorous acid, formic acid, hydrocyanic acid, hydrofluoric acid, hypochlorous acid, and nitrous acid.

The solution is filtered to remove any particulates such as insoluble silicate polymers, etc. This solution is optionally filtered during or prior to introduction into the capillary so as to remove any particulate irregularities, particulates of unknown composition and possibly some insoluble silicate polymers, which may exist within this solution. If the solution is filtered, a disposable syringe filter (not shown) with a mesh size of about 0.45 µm may be used. Other filters may also be used, so long as the mesh size is small enough to remove the particulate irregularities.

The solution is degassed in order to remove any dissolved gas before, during, and/or after hydrolysis, but always before being introduced into a capillary or any channels. For example, helium gas may pass through each reactant for 20 minutes before the reactants are mixed, or the solution may be degassed after hydrolysis by being exposed to a vacuum for 3 minutes.

The solution is introduced into a capillary or similar type of mechanism with a syringe pump or by gas pressure. For example, the solution can also be pumped into a microfluidic channel or a chip. The capillary does not need to be cylindrical, but can be cast into any desired form. The only limitation on such capillary or other mechanism is that it must have comparable or lower hydraulic permeability between the wall of the housing and the monolith as compared to the permeability within the monolith structure.

The ends of the capillary are then sealed. One method of sealing is to place each end of the capillary into silica rubber septa (not shown) or using commercially available fitting unions (not shown) and plugs (not shown). Available commercial parts include Upchurch P882 adapter unions and P551 coned port plugs. Other commercial parts may be used. At this point, the temperature of the solution is raised to between about 20 to 65° C. to initiate polymerization and subsequent gelation. The temperature is maintained for at least 20 hours to cure the monolith.

A capillary useful in connection with the subject invention may be made of fused silica, but may also be made of alumina silica, PEEK, stainless steel, epoxy, ceramics and glass. Useful capillaries currently on the market include 150 μm ID/360 μm OD×~30 cm capillaries clad with polyimide, Teflon® and other polymers. Diameter of the capillary can be between about 20 μm to 1 cm having varying lengths from 1-100 centimeters (cm). The choice of diameter depends primarily on the desired flow rate range that one wants to achieve. One advantage to using fused silica may be increased adhesion of the monolith to the capillary. When the capillary contains silanols which are capable of reacting with the silane monomers, good anchoring support is provided. This differs from the case of polymer monoliths where the capillary surface needs to be first reacted with an appropriate silane which is then capable of further reaction during the polymerization step.

An acid or base pretreatment, or "conditioning", may be used to activate the capillary by exposing the reactive silanol groups in an effort to increase the amount of covalent bonding between the monolith and the pre-treated capillary and create a more stable structure. The following is illustrative of the capillary conditioning reaction:

The above structures are illustrative only. The acceptable molecular formula of fused silica is $SiO_2$ which is a solid amorphous (glass-like) structure. Before capillary conditioning, the surface of fused silica is mostly covered with siloxane bonds (Si—O—Si) and with a fraction of silanol (Si—OH) groups. The conditioning step breaks a siloxane bond into two silanol groups, which can be used as bonding 'anchors' for monoliths. Thus the fused silica surface becomes more reactive as a result of capillary conditioning.

Charged reagents may be covalently bonded to the silica surface of the monolith to change its charge and/or cause a charge to remain permanent over a wide range in pH. Suitable charged reagents useful in connection with the hybrid monoliths of the subject invention include N-trimethoxysilypropyl-N,N,N-trimethylamonium chloride. Silica is uncharged at low pH as the silanol groups are protonated, and therefore without modification is not capable of pumping acid solutions. At pH greater than 4.0, monoliths made of silica are weak acids and are negatively charged.

Figure 8A:
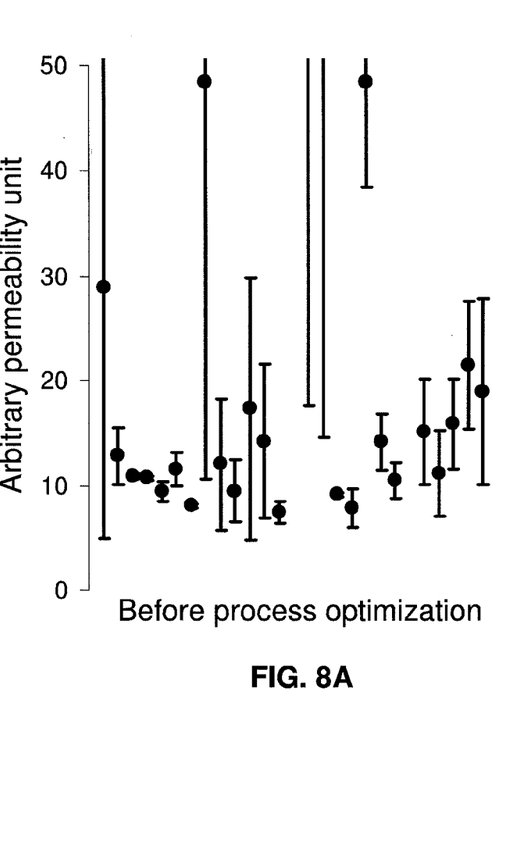
FIG. 8A illustrates arbitrary permeability before process optimization.
Figure 8B:
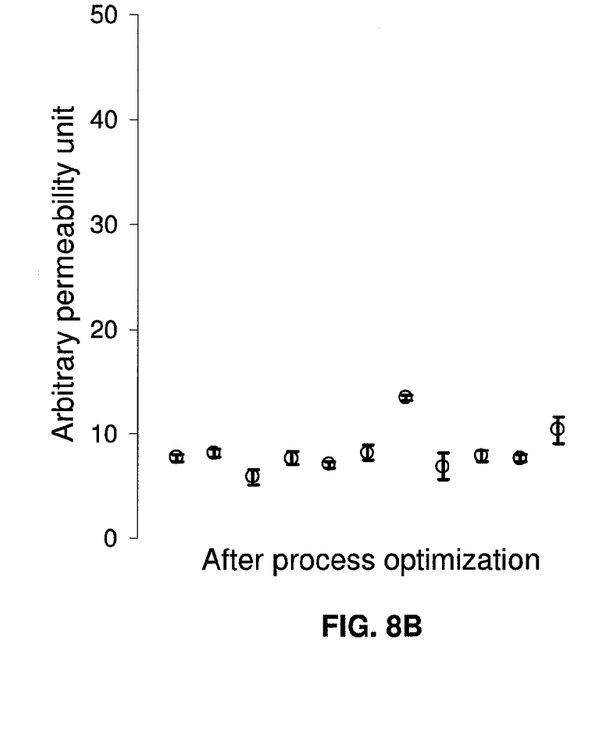
FIG. 8B illustrates arbitrary permeability after process optimization.

The reproducibility of prepared monoliths may be assessed by measuring the hydrodynamic permeability of each monolith. Reproducibility is determined by casting three monolith capillaries from a reactant solution. The average and standard deviation of the permeability is compared among monoliths prepared from several reaction solutions (between-batch reproducibility) and from monoliths synthesized from a single reaction solution (in-a-batch reproducibility). FIGS. 8A and 8B illustrate arbitrary permeability before and after optimization. Monoliths made from the procedure described above typically show similar permeability, suggesting that the preparation process has a good reproducibility.

The surface grafting reaction is as follows:

wherein n is an integer greater than 1 and is determined by when the polymer loses solubility in solution, the random structure contains three subunits A, B, C that may randomly repeat, and the surface of the monolith has residual unreacted silanols.

Noteworthy is that the above structures are provided for illustrative purposes only. The surface grafting reagents can react to the surface silanols (Si—OH) by forming 1, 2, or up to 3 siloxane bonds (Si—O—Si). The monolith is an amorphous structure, thus the exact chemical structure cannot be drawn. Further, the above structure contains three subunits A, B, C that randomly repeat. Also, n is an integer greater than 1 and is determined by various known characterization methods. There are certain standard physical properties that might be measurable including porosity, density, modulus, and glass-transition temperature. MALDI-TOF mass spec may be useful for characterization. Other high molecular weight compounds have been characterized by electrospray.

The hybrid monoliths of the subject invention comprise a compound having the structural Formula I:

wherein:

$X_1$, $X_2$, and $X_3$ vary independently and are selected from the group consisting of OH, alkoxy, alkyl and a bond bridged to the siloxane matrix;

$X_4$ varies independently along the siloxane matrix as [—$SiW_1W_2(CH_2)_mR_2$] and at least one substituent selected from the group consisting of H, alkyl, substituted alkyl, and a bond bridged to the siloxane matrix;

$R_1$ is alkyl, alkenyl, either of which may be optionally substituted;

$R_2$ is a primary, secondary, or tertiary amino group;

$W_1$ and $W_2$ vary independently and are selected from the group consisting of H, alkyl, alkoxy, substituted alkoxy, substituted alkyl, OH, and oxygen, wherein the oxygen is bridged to the siloxane matrix or [—$SiW_1W_2(CH_2)_mR_2$];

m is an integer from 1-15;

n is an integer greater than 1; and the hybrid monolith having molecular weight between about 200 Da to about 100 kDa.

As used herein, the terms below have the meanings indicated.

The term "alkoxy" means a radical comprising an alkyl radical that is bonded to an oxygen atom, such as a methoxy radical. Alkoxy radicals include "lower alkoxy" radicals having one to about ten carbon atoms and often from one to about six carbon atoms. Examples of such radicals include methoxy, ethoxy, propoxy, isopropoxy, butoxy and tert-butoxy.

The term "alkyl", alone or in combination, means an acyclic alkyl radical, linear or branched, preferably containing from 1 to about 10 carbon atoms preferably containing from 1 to about 6 carbon atoms. "Alkyl" also encompasses cyclic alkyl radicals containing from 3 to about 7 carbon atoms, often from 3 to 5 carbon atoms. Said alkyl radicals can be optionally substituted with groups as defined below. Examples of such radicals include methyl, ethyl, chloroethyl, hydroxyethyl, n-propyl, isopropyl, n-butyl, cyanobutyl, isobutyl, sec-butyl, tert-butyl, pentyl, aminopentyl, iso-amyl, hexyl, octyl and the like.

The term "cycloalkyl" embraces radicals having three to ten carbon atoms, such as cyclopropyl cyclobutyl, cyclopentyl, cyclohexyl and cycloheptyl. The term "cycloalkyl" includes a mono- or multi-ringed carbocycle wherein each ring contains three to about seven carbon atoms, preferably three to about five carbon atoms. Examples include radicals such as cyclopropyl, cyclobutyl, cyclopentyl, cyclohexyl, cycloalkenyl, and cycloheptyl. The term "cycloalkyl" further encompasses Spiro systems wherein the cycloalkyl ring has a carbon ring atom in common with the seven-membered heterocyclic ring of the benzothiepine.

The term "heterocyclic" embraces saturated, partially saturated and unsaturated heteroatom-containing ring-shaped radicals, where the heteroatoms may be selected from nitrogen, sulfur and oxygen. Such heterocyclic radicals preferably include ring systems having 3 to 10 members. Examples of saturated heterocyclic radicals include saturated 3 to 6-membered heteromonocylic group containing 1 to 4 nitrogen atoms [e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclic radicals include dihydrothiophene, dihydropyran, dihydrofuran and dihydrothiazole. "Heterocyclic" radicals may have 1 to 3 substituents such as lower alkyl, hydroxy, oxo, amino and lower alkylamino, but include five to six membered heteroaryl radicals.

The term "heteroaryl" embraces unsaturated heterocyclic radicals. Examples of unsaturated heterocyclic radicals, also termed "heteroaryl" radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g., 4H-1,2,4-triazolyl, 1H-1,2,3-triazolyl, 2H-1,2,3-triazolyl, etc.]tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl, etc.], etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 3 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2, 5-thiadiazolyl, etc.] and isothiazolyl; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuryl, benzothienyl, and the like.

The term "optionally substituted" means the proceeding group may be substituted or unsubstituted. When substituted, the substituents of an "optionally substituted" group may include, without limitation, one or more substituents independently selected from the following groups or designated subsets thereof: $(C_1-C_6)$alkyl, $(C_2-C_6)$alkenyl, $(C_2-C_6)$alkynyl, $(C_1-C_6)$heteroalkyl, $(C_1-C_6)$haloalkyl, $(C_2-C_6)$haloalkenyl, $(C_2-C_6)$haloalkynyl, $(C_3-C_6)$cycloalkyl, phenyl, $(C_1-C_6)$ alkoxy, phenoxy, $(C_1-C_6)$haloalkoxy, amino, $(C_1-C_6)$alkylamino, $(C_1-C_6)$alkylthio, phenyl-S—, oxo, $(C_1-C_6)$carboxyester, $(C_1-C_6)$carboxamido, $(C_1-C_6)$acyloxy, H, halogen, CN, $NO_2$, $NH_2$, $N_3$, $NHCH_3$, $N(CH_3)_2$, SH, $SCH_3$, OH, $OCH_3$, $OCF_3$, $CH_3$, $CF_3$, $C(O)CH_3$, $CO_2CH_3$, $CO_2H$, $C(O)$ $NH_2$, pyridinyl, thiophene, furanyl, (C1-C6)carbamate, and ($C_1$-$C_6$)urea. Two substituents may be joined together to form a fused five-, six-, or seven-membered carbocyclic or heterocyclic ring consisting of zero to three heteroatoms. An optionally substituted group may be unsubstituted (e.g., —CH2CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$).

The amino groups of Formulas I and II, as disclosed herein, may be derived from the corresponding primary, secondary and tertiary amines identified below. These amines are exemplary and thus not limiting.

Primary amines, as disclosed herein, may refer to straight chain primary amines alkyl amines such as methylamine, ethylamine, propylamine, isopropylamine, butylamine, sec-butylamine, iso-butylamine, tert-butylamine, pentylamine, 1,1-dimethylpropylamine, 1,2-dimethylpropylamine, 1-ethylpropylamine, 2-methylbutylamine, isopentylamine, hexylamine, 1,3-dimethylbutylamine, 3,3-dimethylamine, heptylamine, 2-aminoheptane, octylamine, 1,5-dimethylhexylamine, 2-ethylhexylamine, 1-methylheptylamine, tert-octylamine, nonylamine, decylamine, undecylamine, dodecylamine, tridecylamine, tetradecylamine, pentadecylamine, hexadecylamine, heptadecylamine, octadecylamine, nonadecylamine, eicosylamine, any of which may be optionally substituted.

Primary and secondary amines, as disclosed herein, may include to straight chain benzylamines, such as benzylamine, N-methylbenzylamine, N-ethylbenzylamine, N-propylbenzylamine, N-butylbenzylamine, N-pentylbenzylamine, N-hexylbenzylamine, N-heptylbenzylamine, N-octylbenzylamine, N-nonylbenzylamine, N-decylbenzylamine, N-undecylbenzylamine, N-dodecylbenzylamine, N-tridecylbenzylamine, N-tetradecylbenzylamine, N-pentadecylbenzylamine, N-hexadecylbenzylamine, N-heptadecylbenzylamine, N-octadecylbenzylamine, dibenzylamine, N-isopropylbenzylamine, any of which may be optionally substituted.

Primary and secondary amines, as disclosed herein, may include to aniline derivatives such as aniline, N-methylaniline, N-ethylaniline, N-propylaniline, N-butylaniline, N-pentylaniline, N-hexylaniline, N-heptylaniline, N-octylaniline, N-nonylaniline, N-decylaniline, N-undecylaniline, N-dodecylaniline, N-tridecylaniline, N-tetradecylaniline, N-pentadecylaniline, N-hexadecylaniline, N-heptadecylaniline, N-octadecylaniline, any of which may be optionally substituted.

Primary and secondary amines, as disclosed herein, may include to aryl and heteroaryl amines such as phenylamines, such as phenethylamine, N-methylphenethylamine, 4-methylphenethylamine, 3-phenylpropylamine, 1-methyl-3-phenylpropylamine, and 4-phenylbutylamine, any of which may be optionally substituted. Secondary heteroaryl amines may include, for example, benzimidizole, 1-H-indazole, carbazole, indole, indoline, 1-H tetrazole, 1,2,4-triazole, pyrrole, imidazole, and 1,2-diazole, any of which may be optionally substituted.

Secondary amines, as disclose herein, may include to heterocyclic amines such as pyrrolidine, 2-methylpiperidine, 3-methylpiperidine, 4-methylpiperidine, 2-pyrroline, 3-pyrroline, pyrazolidine, imidazolidine, 2-pyrazoline, 2-imidazoline, imidazoline-2-thione, 1,2,3-triazole, 1-H-pyridin-2-one, azepine, 5-H-1,2,5-oxathiazole, 1,2,4-oxadiazine, 2-H-1,2-oxazine, any of which may be optionally substituted.

Secondary and tertiary amines, as disclosed herein may refer to straight chain secondary and tertiary amines such as dimethylamine, trimethylamine, diethylamine, triethylamine, dipropylamine, tripropylamine, dibutylamine, tributylamine, dipentylamine, and tripentylamine.

Secondary and tertiary amines, as disclose herein, may include to straight chain mixed amines, for example, N-methylethylamine, N,N-dimethylethylamine, and N-methyldiethylamine, any of which may be optionally substituted.

Primary, secondary, and tertiary amines, as disclosed herein, may include to diamines, for example, N,N-dimethylethylenediamine, N,N'-dimethylethylenediamine, N,N-dimethyl-N'-ethylenediamine, any of which may be optionally substituted.

Primary, secondary and tertiary amines, as disclosed herein, may include to cycloalkyl amines, for example, cyclohexylamine, N-methyl cyclohexylamine, N,N-dimethylcyclohexylamine, N,butylcyclohexylamine, N,N-dibutylcyclohexylamine and respective cyclobutyl, pentyl, heptyl and octyl-systems, any of which may be optionally substituted.

Hence, illustrative of the grafted hybrid monolith is the following composition:

hybrid monolith wherein n is an integer greater than 1 and is determined by when the polymer loses solubility in solution, the random structure contains three subunits A, B, C that may randomly repeat, and the surface of the monolith has residual unreacted silanols and siloxanes.

Figure 6A:
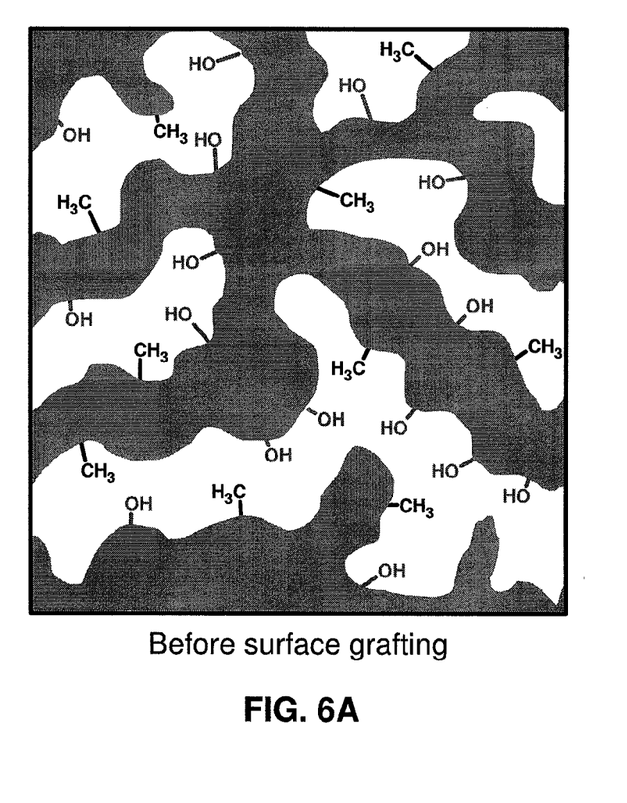
FIG. 6A is an illustration of the monolith surface before the grafting reaction.
Figure 6B:
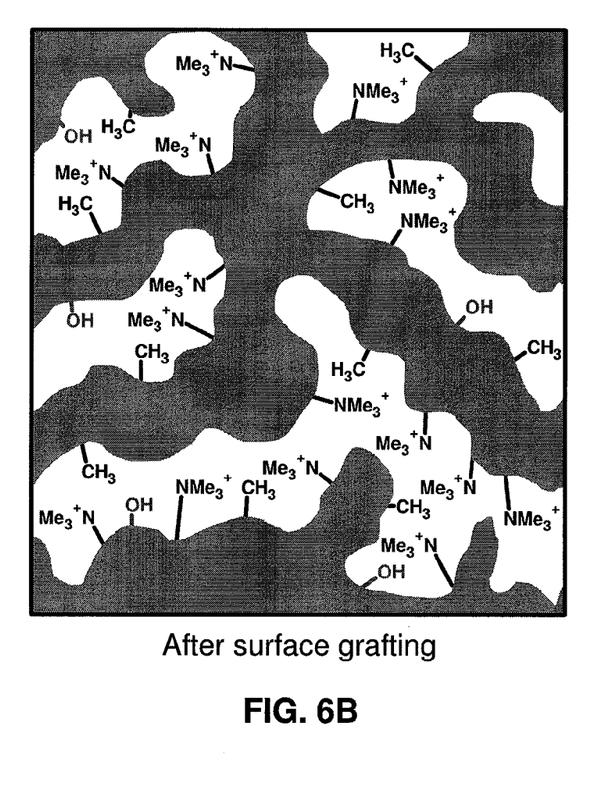
FIG. 6B is an illustration of the monolith surface after surface grafting.

The monolith charge may be made permanently positive (by incorporation of a quaternary amine structure) and remains as such under operating conditions of pH between about 2 to about 9. In addition, FIGS. 6A and 6B show the surface grafting reaction changes that the surface charge on the monoliths by replacing the surface silanol groups into permanently charged quaternary amine groups (—NMe$_3^+$). Any of the above listed amines may also be made permanently positively charged by quaternization of nitrogen with an alkylating agent, for example CH$_3$X. X may be any halogen or other leaving group.

The monolith may not have a permanent charge. Alternatively, amine structures may be made positively charged by adjustment of pH below 7, for example.

The monolith of the subject invention is characterized by a continuous, interconnected pore structure of large macropores. The macropore size can be changed independent of the skeleton size without causing bed instability. The monolith has high flow resistivity having pore sizes less than 1 micron.

The EK pumps of the subject invention are stable. The EK pump of FIG. 1 has been shown to be stable for more than 1400 hours with less than 20 percent decrease in performance.

The EK pump of the subject invention provides improved reproducibility. The production of monoliths in capillaries is reproducible in terms of pore size and/or porosity. Briefly, a piece of monolith in a capillary was pressurized with water at up to 5000 psi, and the resultant flow rate was measured. The flow rates become smaller as the porosity is decreased and the length of the capillary is increased (assuming that the pore sizes are consistent along the length). Flow resistivity is defined by dividing the applied pressure by the EK pump length and by the flow rate. Higher flow resistivity likely reflects a reduction in average pore size. Reproducibility is determined by casting three monolith capillaries from a reactant solution. The average and standard deviation of the flow resistivity is compared among monoliths prepared from several reaction solutions (between-batch reproducibility) and from monoliths synthesized from a single reaction solution (in-a-batch reproducibility). The monolith preparation process has been optimized for reproducible production of hybrid monoliths. The process reproducibility has been improved by the precise temperature control and by removing dissolved or entrapped gas in the reaction mixtures filled in capillaries or similar channels.

Figure 4:
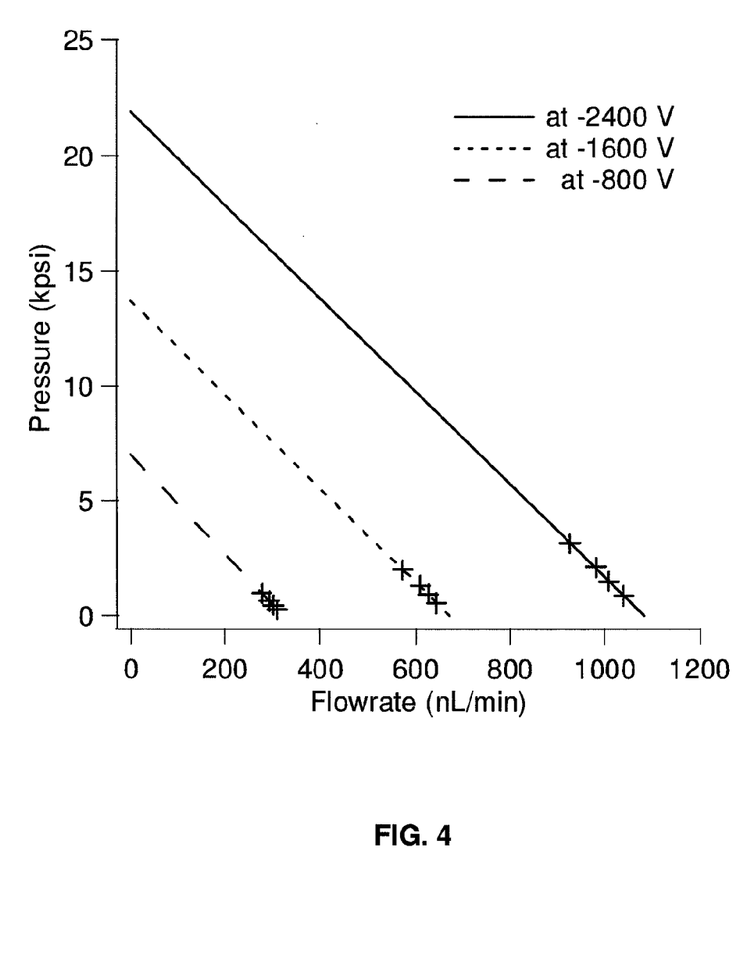
FIG. 4 is a chart depicting the results of the EK pump performance.

The EK pumps of the subject invention have the ability to pump solutions of pH between about 2 to about 9. As shown in FIG. 4, the EK pump has maximum flow rate of 1.1 μl/min at the applied voltage of −2400 V using 0.1% acetic acid as a pumping fluid. At the same operating conditions, it can generate 840 nl/min at 5000 psi or 340 nl/min at 15000 psi. The EK pump of the subject invention can generate higher flow rate at higher applied voltages, by utilizing different pumping fluids and so on. Also, the maximum flow rate might be increased by improved surface grafting. Maximum flow rate is determined by the diameter of the EK pump. Superficial linear velocity is defined as flow rate divided by the cross-sectional area of the tube ($F/A=F/\pi r^2$). For example, a flow rate of 1.1 uL/min in a 150 um ID tube gives a linear velocity of $([(1.1\ uL/min)(min/60\ sec)(cm^3/1000\ uL)]/[(\pi)(75\times10^{-4}\ cm)^2])\sim 0.1$ cm/s. Flow rate is also directly proportional to the applied voltage. The maximum applied voltage depends on two parameters: when arcing occurs, and when too much heat is generated.

The EK pumps of the present invention are compatible with chip formats. A monolith is formed from a solution which does not have particular form. Thus the monolith can be formed into any given shape. For chip applications, monoliths are formed at atmospheric pressure by filling a channel and polymerizing the monomers. See e.g. Ishida, A., et al., Reversed-phase Liquid Chromatography on a Microchip With Sample Injector and Monolithic Silica Column, J. Chromatogr. A 1132 (2006) 90-98.

Figure 7:
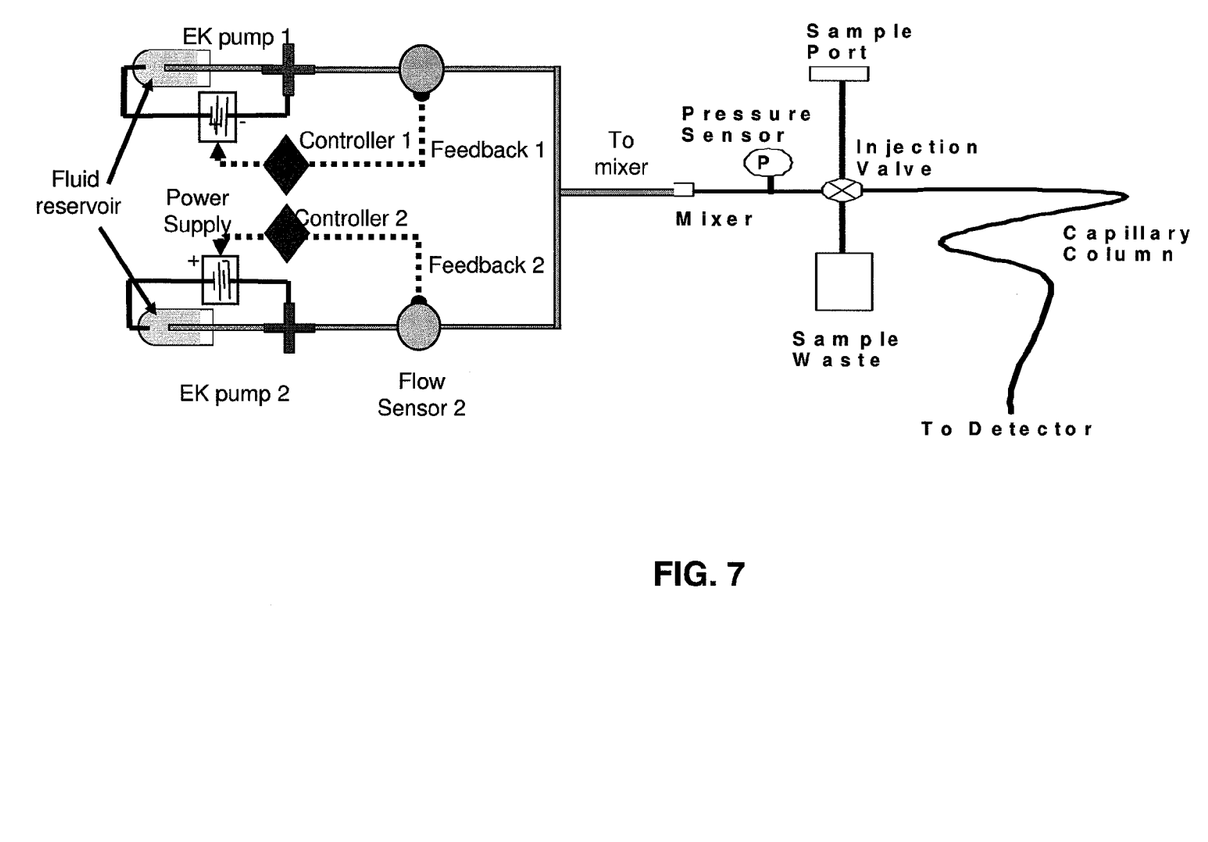
FIG. 7 is a diagram of an HPLC system using the EK pump of the subject invention.

The EK pumps of the present invention are also useful in connection with HPLC systems. The EK pump is a device that delivers liquid against a relatively high back pressure. Current HPLC systems employ mechanical pumps to achieve pressures between 1000 and 10,000 psi (or greater) depending on the dimensions and particle size of the column. The EK pump can replace the mechanical pump which can provide benefits of pulseless flow, smaller size and reduced manufacturing costs. FIG. 7 provides a typical EK pump for an HLPC system.

To test the EK pump of the subject invention, several different test parameters are reviewed including: (a) flow factor (nL/min/V); (b) EK factor (psi/volt); (c) current (μA); and lifetime in hours. The flow factor, a theoretical parameter equivalent to the flow when there is no pressure load applied to the pump, is a measure of the pumping capacity. Zeta potential is a measure of the surface charge density. Thus, the higher the zeta potential, the greater the flow rate.

EK factor is a measure of the maximum pressure attainable from an EK pump operating at a specific applied voltage. The current is related to the conductivity of the solvent and is also related to the rate of gas formation and joule heating.

Figure 5:
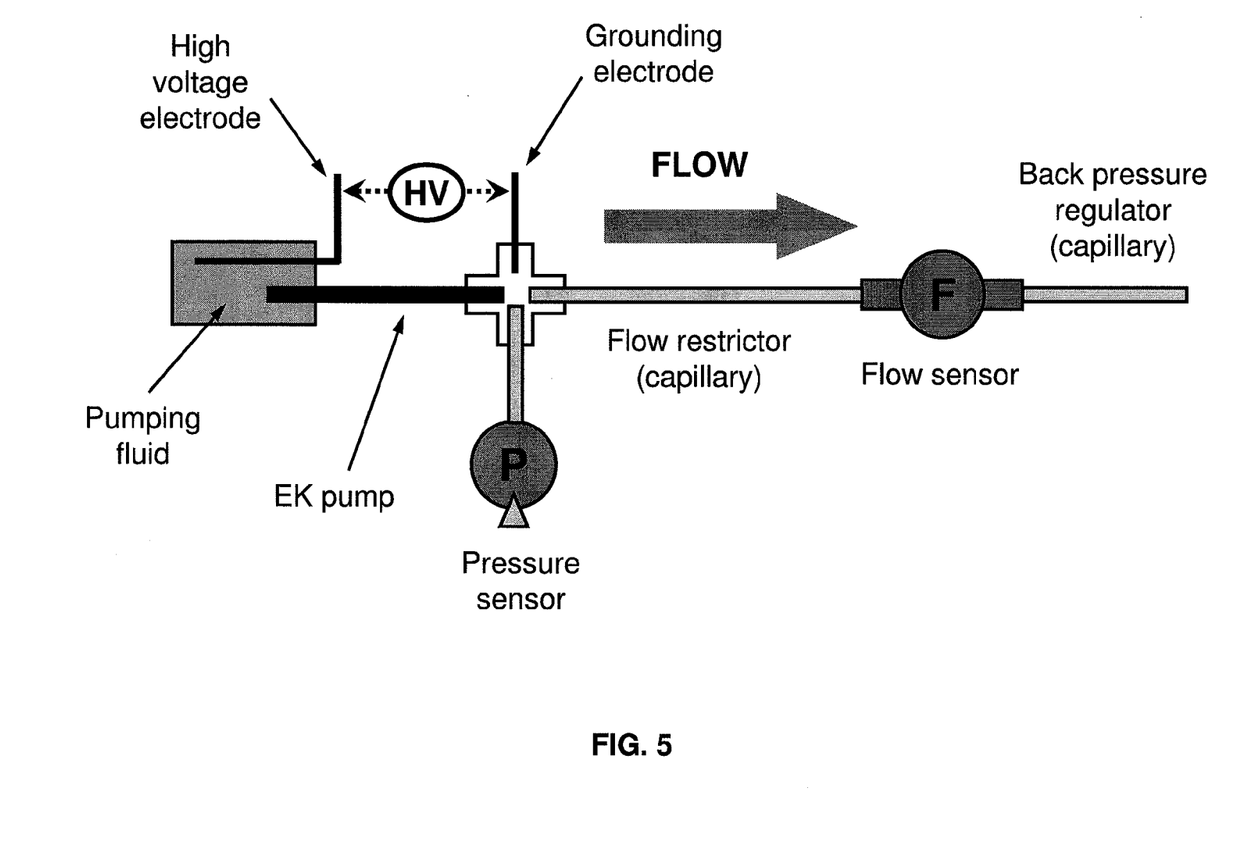
FIG. 5 is an illustration of an EK pump test station.

FIG. 5 is a diagram showing a configuration for testing the EK pump of the subject invention. The electrical current is provided by an electrode placed in the fluid reservoir. A first end of the EK pump is placed in the fluid and a second end is connected to a cross connector. The fluid outlet of the cross connector is connected to a capillary restrictor tube, and the other fittings of the cross connector are attached to a pressure sensor and a ground electrode, respectively. The outlet of the restrictor is connected to a flow sensor. The flow sensor is connected to a waste line.

FIG. 4 provides a plot charting the results obtained with the monolith EK pump operated at several voltages (−800, −1600 and −2400 V). The polarity of the applied voltage is important in our examples, since the reversal of the polarity will results in reversal of the flow direction. Flow rate and backpressure using a given restrictor at a specified voltage are measured with the flow sensor and the pressure sensor as shown in FIG. 5. Different backpressures for the system were obtained by using capillary restrictors of different dimensions as shown in FIG. 5. Flow rate and backpressure using a given restrictor and specified voltage are measure with the flow sensor and pressure is monitored as shown in FIG. 5.

The invention is further illustrated by the following examples.

Example 1

Pretreatment of Capillary

A polyimide coated fused silica capillary (Polymicro Technologies, Phoenix, Ariz., P/N TSP150375) is conditioned with base and acid. The capillary is rinsed by flowing acetone at approximately 50 μL/min for about 2 hours followed by a 1M NaOH rinse at approximately 50 μL/min for about 2 hours. The capillary is then sealed to retain the 1M NaOH and then heated in an oven at approximately 80° C. for about 2 hours. Subsequently, the capillary is removed from the oven and cooled to room temperature. Then the capillary is rinsed with 1M HCl at approximately 50 μL/min for about 2 hours. The capillary is finally rinsed with deionized water at approximately 50 μL/min for several hours, until all the acid is washed out. Although specific time and flow rates have been provided for each step of the capillary pre-treatment, these values are not important so long as the rinsing volume is much greater than the inner volume of the capillary tube.

Example 2

Preparation of a Hybrid Monolith

In a one step method, MTMS hydrolysis and condensation proceeds at a single catalyst concentration using an acid catalyst to achieve conditions where the pH was below the IEP of the silanol groups respectively. Between about 1.4 to 1.8 ml methanol is mixed in solution with about 10 ml of MTMS and about 2.6 milliliters of 1 molar $HNO_3$. The solution is stirred for five minutes at a temperature between 0 to 4° C. where hydrolysis take place. The solution is pumped into the pre-treated capillary of example 1 and is sealed. The capillary is maintained in a water bath at approximately 40° C. for about 20-24 hours. In this example, the pretreated capillary's inner surface is SiOH. At the increased temperature, the condensation reactions takes place and polymerization/gelation takes place within the capillary.

Example 3

Grafting of the Monolith

A charged reagent, N-trimethoxysilypropyl-N,N,N-trimethylamonium chloride plus ethanol plus 5% acetic acid as a catalyst (total acid concentration=1%) is pumped through the hybrid monolith of Example 2 and cured at 40° C. for a few hours or longer. N-trimethoxysilypropyl-N,N,N-trimethylamonium chloride is covalently bonded to the silica surface of the monolith.

Example 4

Testing of the EK Pump

The monolith of Example 3 was tested as an EK pump using the setup shown in FIG. 5. The resulting current, flow rate and pressure were measured at different applied voltages and with different flow restrictor elements. Flow factor and EK factor were derived from the pressure vs. flow rate plot shown in FIG. 4. A straight line connecting all values at a given voltage creates two intercepts. The intercepts are divided by the applied voltage to get the two voltage-independent factors. The results are depicted in FIG. 4. The maximum operating pressure at −2400 V is about 22,000 psi, 14000 psi at −1600 V and 7000 psi at −800 V. The average EK factor is thus 9 psi/V. The averaged EK factors along with the standard errors are plotted versus operation time to yield the lifetime plot shown in FIG. 1.

Between each points in FIG. 1 (50 to 150 hours interval), the EK pump was continuously operating against a fixed flow restrictor as shown in FIG. 5. The applied voltage was routinely changed from 0 V to −3000 V at 10 minute intervals with a 500 V step down and up. The back pressure was normally less than 5000 psi. The resulting flow rate/pressure plots upon the potential steps are not provided.

We claim the following:

1. A hybrid monolith comprising a compound of the structural Formula I:

$$HO \left[ \begin{array}{c} OX_4 \\ | \\ Si-O \\ | \\ R_1 \end{array} \right]_n SiX_1X_2X_3$$

wherein:
$X_1$, $X_2$, and $X_3$ vary independently and are selected from the group consisting of OH, alkoxy, alkyl and a bond bridged to a monolith comprising a siloxane matrix and a monolith surface having silanol groups;
$X_4$ varies independently along the monolith as [—$SiW_1W_2(CH_2)_mR_2$] and at least one substituent selected from the group consisting of H, alkyl, substituted alkyl, and a bond bridged to the monolith surface;
$R_1$ is alkyl, or alkenyl, either of which may be optionally substituted;
$R_2$ is a primary, secondary, or tertiary amino group;
$W_1$ and $W_2$ vary independently and are selected from the group consisting of H, alkyl, alkoxy, substituted alkoxy, substituted alkyl, OH, and oxygen, wherein the oxygen is bridged to the siloxane matrix or [—$SiW_1W_2(CH_2)_mR_2$];
m is an integer from 1-15; and
n is an integer greater than 1,
wherein silanol groups on the surface of the monolith are substantially replaced by quaternary amine groups to generate the positive surface charge stable under operating conditions of pH between about 2 and 9.

2. A hybrid monolith having a surface comprising a compound having the following random structure:

[Structure showing hybrid monolith with subunits {A}, {B}, {C}]

hybrid monolith wherein n is an integer greater than 1 and is determined by when the hybrid monolith loses solubility in solution, the random structure contains three subunits A, B, C that may randomly repeat, and the surface of the hybrid monolith has residual unreacted silanols and substantially comprises charged quaternary amine groups that generate a stable positive charge on the surface under operating conditions of pH between about 2 and 9.

3. A hybrid monolith prepared by a process comprising the steps of:
mixing a hydrolysable alkoxysilane monomer with an acidic catalyst and methanol wherein the amount of methanol in the reaction is between about 10 to 18 percent by volume to produce a monolith having a monolith surface; and
grafting the monolith surface to produce the hybrid monolith having a stable positive surface charge comprising a compound of the structural Formula I:

$$HO \left[ \begin{array}{c} OX_4 \\ | \\ Si-O \\ | \\ R_1 \end{array} \right]_n SiX_1X_2X_3$$

wherein:
$X_1$, $X_2$, and $X_3$ vary independently and are selected from the group consisting of OH, alkoxy, alkyl and a bond bridged to the monolith;
$X_4$ varies independently along the monolith as [—$SiW_1W_2(CH_2)_mR_2$] and at least one substituent selected from the group consisting of H, alkyl, substituted alkyl, and a bond bridged to the monolith, wherein $X_4$ provides a positive surface charge on the hybrid monolith;
$R_1$ is alkyl, or alkenyl, either of which may be optionally substituted;

$R_2$ is a primary, secondary, or tertiary amino group;

$W_1$ and $W_2$ vary independently and are selected from the group consisting of H, alkyl, alkoxy, substituted alkoxy, substituted alkyl, OH, and oxygen, wherein the oxygen is bridged to the monolith or $[-SiW_1W_2(CH_2)_mR_2]$;

m is an integer from 1-15; and n is an integer greater than 1, wherein silanol groups on the monolith are substantially replaced by quaternary amine groups to generate a stable positive surface charge under operating conditions of pH between about 2 and 9.

* * * * *